United States Patent
Oono et al.

(10) Patent No.: US 9,073,692 B2
(45) Date of Patent: Jul. 7, 2015

(54) MEDICINE ISSUING DEVICE AND CONTAINER IDENTIFYING DEVICE

(71) Applicant: PANASONIC HEALTHCARE HOLDINGS CO., LTD., Tokyo (JP)

(72) Inventors: Masaharu Oono, Ehime (JP); Taizo Isshiki, Ehime (JP); Michimori Nakano, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 0 days.

(21) Appl. No.: 14/090,449

(22) Filed: Nov. 26, 2013

(65) Prior Publication Data

US 2014/0217165 A1 Aug. 7, 2014

Related U.S. Application Data

(63) Continuation of application No. PCT/JP2012/004020, filed on Jun. 21, 2012.

(30) Foreign Application Priority Data

Jun. 27, 2011 (JP) ................. 2011-141363

(51) Int. Cl.
*G06K 19/00* (2006.01)
*B65G 1/137* (2006.01)
(Continued)

(52) U.S. Cl.
CPC ................. *B65G 1/1371* (2013.01); *A61J 3/00* (2013.01); *G07F 11/165* (2013.01); *G07F 17/0092* (2013.01); *A61M 2205/6072* (2013.01); *B65G 1/06* (2013.01)

(58) Field of Classification Search
USPC .................. 235/375, 381, 435, 439, 451, 462
See application file for complete search history.

(56) References Cited

U.S. PATENT DOCUMENTS 5,774,865 A 6/1998 Glynn
5,852,590 A 12/1998 de la Huerga
(Continued)

FOREIGN PATENT DOCUMENTS

CN 101262838 9/2008
JP 62-173482 7/1987
(Continued)

OTHER PUBLICATIONS

Office Action issued Aug. 18, 2014 in corresponding Chinese Application No. 201280020297.7, with English translation.
(Continued)

*Primary Examiner* — Matthew Mikels
(74) *Attorney, Agent, or Firm* — Wenderoth, Lind & Ponack, L.L.P.

(57) ABSTRACT

This medicine issuing device is a container identifying device for identifying tubular medicine containers (1,2,3) provided with identifying marks (4,5,6) on their external circumference, said medicine issuing device comprising: an operation component (7) that takes the medicine containers (1,2,3) out of a cassette (403); a movement path component (8) that moves the medicine containers (1,2,3) taken out by the operation component (7) to an identification position (9); a container rotation component (10) that rotates the medicine containers (1,2,3) that were moved to a specific identification position (9) by the movement path component (8), around an outer peripheral face; and an identifying mark reader (11) that reads the identifying marks (4,5,6) of the medicine containers (1,2,3) rotated by the container rotation component (10).

17 Claims, 18 Drawing Sheets

(51) Int. Cl.
*A61J 3/00* (2006.01)
*G07F 11/16* (2006.01)
*G07F 17/00* (2006.01)
*B65G 1/06* (2006.01)

(56) References Cited

U.S. PATENT DOCUMENTS

| | | | |
|---|---|---|---|
| 6,068,437 | A | 5/2000 | Boje et al. |
| 6,150,942 | A | 11/2000 | O'Brien |
| 6,370,841 | B1 | 4/2002 | Chudy et al. |
| 6,529,446 | B1 | 3/2003 | de la Huerga |
| 2002/0063036 | A1 | 5/2002 | Wunscher et al. |
| 2003/0160698 | A1 | 8/2003 | Andreasson et al. |
| 2004/0008123 | A1 | 1/2004 | Carrender et al. |
| 2004/0112911 | A1 | 6/2004 | Kim |
| 2008/0029530 | A1* | 2/2008 | Yuyama et al. .................. 221/2 |
| 2008/0115456 | A1* | 5/2008 | Kim ................. 53/154 |
| 2008/0118335 | A1 | 5/2008 | Ishida et al. |
| 2008/0283596 | A1 | 11/2008 | Ishida |
| 2010/0147868 | A1 | 6/2010 | Yuyama et al. |
| 2012/0175380 | A1 | 7/2012 | Nishimura et al. |

FOREIGN PATENT DOCUMENTS

| | | |
|---|---|---|
| JP | 2-28406 | 1/1990 |
| JP | 10-81407 | 3/1998 |
| JP | 10-83476 | 3/1998 |
| JP | 2000-81439 | 3/2000 |
| JP | 2002-150217 | 5/2002 |
| JP | 2003-81429 | 3/2003 |
| JP | 2004-37259 | 2/2004 |
| JP | 2005-125013 | 5/2005 |
| JP | 2005-237713 | 9/2005 |
| JP | 2007-209599 | 8/2007 |
| JP | 4467850 | 5/2010 |
| JP | 4759099 | 8/2011 |
| WO | 2011/007559 | 1/2011 |

OTHER PUBLICATIONS

International Search Report issued Aug. 7, 2012 in International (PCT) Application No. PCT/JP2012/004020.

* cited by examiner

MEDICINE ISSUING DEVICE AND CONTAINER IDENTIFYING DEVICE

TECHNICAL FIELD

The present invention relates to a medicine issuing device and a container identifying device for identifying medicine containers, for example.

BACKGROUND ART

Conventional container identifying devices of this type have been widely used in medicine issuing devices, for example, and have had the following configuration.

A conventional medicine issuing device comprised a cassette in which are loaded a plurality of tubular medicine containers provided with identifying marks on the outer peripheral face, a container removal head for taking medicine containers out of this cassette, and a placement component for placing in a tray the medicine containers taken out by this container removal head (see Patent Literature 1 below, for example).

CITATION LIST

Patent Literature

Patent Literature 1: Japanese Laid-Open Patent Application 2007-209599

SUMMARY

Technical Problem

With the conventional configuration above, the medicine containers are taken out of the cassette by the container removal head, and then the medicine containers are placed in a tray by the placement component, but sometimes the right container could not be removed from the cassette by the container removal head.

Specifically, if the wrong medicine container was loaded into the cassette, there was no means for identifying that the container held medicine that was different from the desired medicine, so it could not be recognized that the proper container had not been taken out of the cassette, and there was the risk that it would remain that way in the tray.

In view of this, it is an object of the present invention to provide a medicine issuing device and a container identifying device with which it is possible to recognize whether or not the right container has been taken out of the cassette, and the desired container can be taken out more accurately.

Solution to Problem

To achieve the stated object, the medicine issuing device of the present invention comprises a cassette, an operation component, a movement path component, a container rotation component, and an identifying mark reader. The cassette is loaded with a plurality of tubular medicine containers provided with identifying marks on their outer peripheral face of the tubular medicine containers. The operation component takes the medicine containers out of the cassette. The movement path component moves the medicine containers taken out by the operation component to a specific identification position. The container rotation component rotates the medicine containers around the outer peripheral face until the reading of the identifying marks on the medicine containers is complete at the identification position. The identifying mark reader reads the identifying marks on the medicine containers rotated by the container rotation component.

With the present invention, a medicine container that has been taken out by the operation component is moved by the movement path component to a specific identification position. At this identification position, the medicine container is rotated around the outer peripheral face until the reading of the identifying marks is complete.

Consequently, the identifying marks on the medicine container can be reliably read at the identification position. This allows the type of medicine container that has been taken out to be accurately identified. Thus, the proper medicine container can be taken out of the cassette by the container removal head, and the proper medicine container can be placed at the specified location. This avoids a situation in which the wrong medicine is dispensed, and allows risk management to be carried out more effectively.

The container identifying device of the present invention is for identifying a tubular container provided with an identifying mark on its outer peripheral face, said container identifying device comprising an operation component, a movement path component, a container rotation component, and an identifying mark reader. The operation component takes a medicine container out of a cassette filled in with a plurality of the medicine containers. The movement path component moves the containers taken out by the operation component to a specific identification position. The container rotation component rotates the containers around the outer peripheral face of the containers until the reading of the identifying marks on the containers is complete at the identification position. The identifying mark reader reads the identifying marks on the containers rotated by the container rotation component.

With the present invention, a container that has been taken out by the operation component is moved to a specific identification position by the movement path component. At this identification position, the container is rotated around the outer peripheral face by the container rotation component until the reading of the identifying marks is complete.

This allows the identifying marks on the container to be reliably read at the identification position. Thus, the type of container that has been taken out can be accurately identified. This allows the container removal head to take the right container out of the cassette and place in the intended position.

DESCRIPTION OF EMBODIMENTS

A case in which the container identifying device pertaining to an embodiment of the present invention is applied to a medicine issuing device 101 will now be described through reference to the drawings.

Embodiment 1

Figure 1:
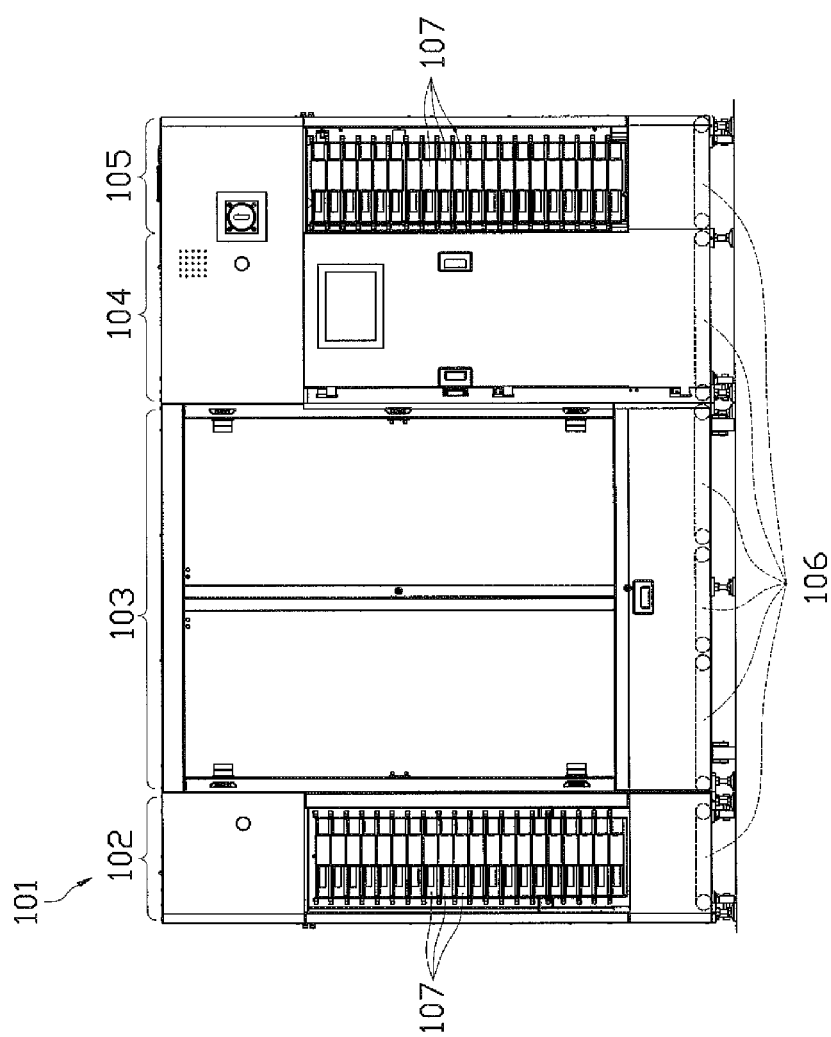
FIG. 1 is a front view of the medicine issuing device pertaining to an embodiment of the present invention.

FIG. 1 is a front view of the outer appearance of the medicine issuing device 101.

The medicine issuing device 101 comprises an empty tray unit 102, a medicine dispensing unit 103, a printer unit 104, a filled tray unit 105, and a tray conveyor 106 that links these together.

The empty tray unit 102 holds empty trays 107 placed thereon for carrying various kinds of medicine, and supplies empty trays 107 to the tray conveyor 106 provided below.

In this embodiment, the empty tray unit 102 is equipped with a door made of transparent plastic, glass, or the like on its front side. This makes it easy to check how many trays 107 are inside the empty tray unit 102. The empty tray unit 102 does not necessarily have to have a door (cover) such as this, and the trays 107 may be held so that they are exposed.

The medicine dispensing unit 103 separately stores various kinds of medicine, and dispenses the medicine required for each patient on the basis of pharmaceuticals (such as prescription data), to the empty trays 107 conveyed from the empty tray unit 102 by the tray conveyor 106.

The medicine dispensing unit 103 is provided with numerous cassettes 403 that store medicines by type, and dispensing means, etc., for taking out the desired medicine based on pharmaceuticals from the cassettes 403 and placing the medicines on the trays 107. The detailed configuration of the medicine dispensing unit 103 will be discussed below.

The "medicine" is what is being prescribed, and encompasses, for example, injections, drops, internal medicines, plasters, and suppositories. The package of the medicine is typically an ampoule or plastic bottle in the case of an injection, an infusion bag in the case of drops, or a small bottle, SP pouch, PTP pouch, or the like in the case of internal-use tablets, powders, and so forth.

The printer unit 104 is equipped with a printer that prints medicine labels for various kinds of drug and prescriptions listing the details of the drug prescription including the injector prescription and the other prescriptions, on the basis of prescription data. The printer unit 104 also dispenses printed prescriptions and medicine labels to the trays 107 that have been conveyed by the tray conveyor 106 from the medicine dispensing unit 103.

In this embodiment, the front of the printer unit 104 is covered with an openable door made of opaque metal or plastic in order to prevent dust or foreign matter from the outside from entering the printer unit 104. The printed matter produced by the printer unit 104 here contains personal information and is highly confidential. Therefore, a personal verification means for identifying who is opening and closing the door may be provided so that only an authorized person can open and close the door. The medicine dispensing unit 103 and the printer unit 104 may also be disposed in reverse order.

The filled tray unit 105 receives the trays 107 sent by the tray conveyor 106 from the printer unit 104, and holds the trays placed on it. At this point the various medicines, injection prescriptions, medicine labels, and so forth are placed on the trays 107.

The filled tray unit 105 is similar to the empty tray unit 102 in that it has an openable door made of transparent plastic, glass, or the like on its front side. Since the door is made of transparent plastic or the like, it is easy to check how many filled trays are inside the filled tray unit 105. The door provided on the front also prevents the trays 107 carrying the medicines from falling out, which prevents damage to the medicines in the trays. From a functional standpoint, the filled tray unit 105 does not necessarily have to have a door (cover), and the trays 107 may be held so that they are exposed. The trays 107 placed in the filled tray unit 105 are transferred to a cart or the like and carried by a nurse, pharmacist, or the like to where the physician or patient is.

The tray conveyor 106 uses a conveyor belt or other such means to convey the trays 107 from the empty tray unit 102 through the medicine dispensing unit 103 and the printer unit 104 to the filled tray unit 105. In the medicine issuing device 101 in this embodiment, the tray conveyer 106 is provided independently from the various units, below the units.

The tray conveyor 106 receives the empty trays 107 from the empty tray unit 102 and conveys them in a specific direction. When the trays 107 have moved to the medicine dispensing unit 103, drugs are dispensed, and when the trays 107 have been moved to the printer unit 104, prescriptions or medicine labels are dispensed. The tray conveyor 106 then passes the trays 107 carrying the drugs and prescriptions or medicine labels to the filled tray unit 105.

By thus providing the tray conveyor 106 in a row below the various units, the layout of the trays 107, drug dispensing, printed matter dispensing, and the sending out of the trays 107 can all proceed simultaneously and in parallel at the various units. As a result, the drug issuing operation can be carried out more quickly. The configuration and operation of the tray conveyor 106 will be described in detail below.

Next, the configuration of the tray conveyor 106 will be described through reference to FIGS. 2 and 3.

Figure 2:
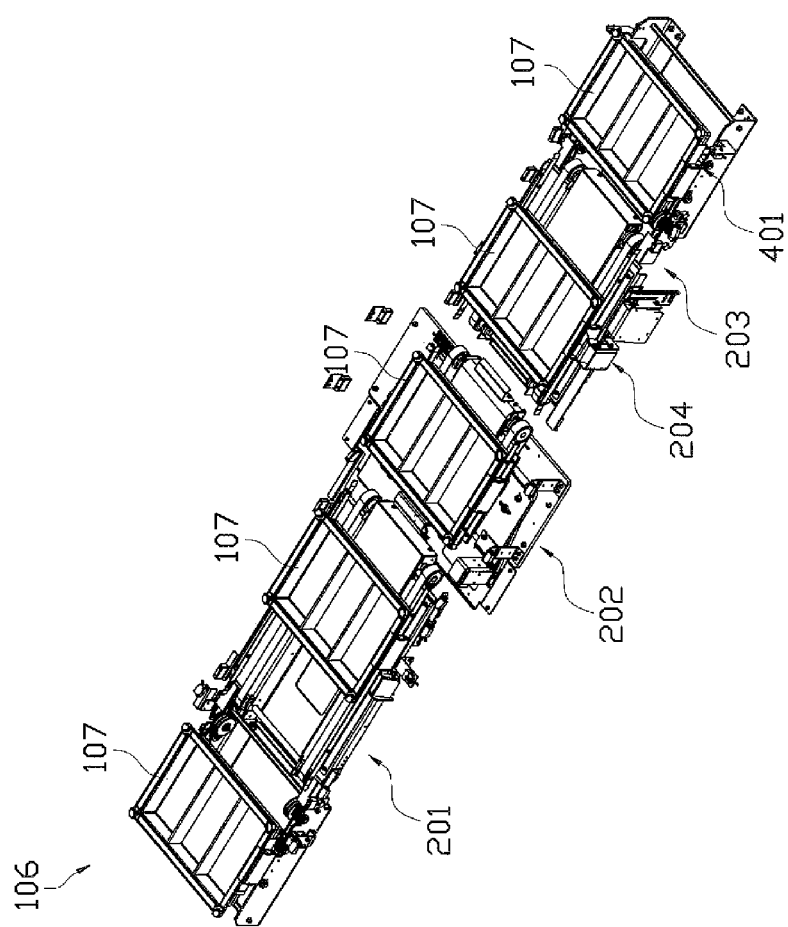
FIG. 2 is an oblique view of the configuration of the main parts of the medicine issuing device in FIG. 1.
Figure 3:
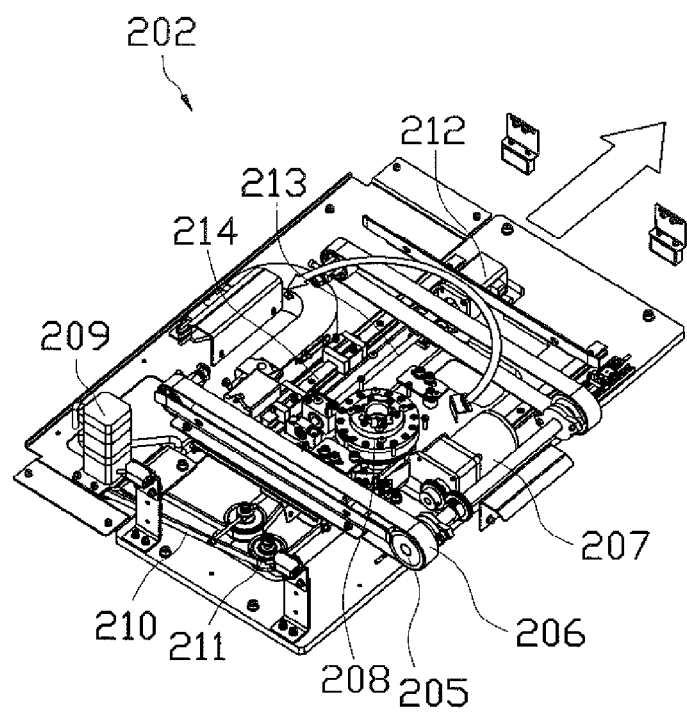
FIG. 3 is an oblique view of the configuration of the main parts of the medicine issuing device in FIG. 1.

FIG. 2 is an oblique view of the configuration of the tray conveyor 106 at the lower part of the medicine dispensing unit 103, and FIG. 3 is an oblique view of the configuration of a second conveyor 202 (see FIG. 3) that is able to turn and is included in the tray conveyor 106.

FIGS. 2 and 3 show the state when the medicine issuing device 101 in FIG. 1 is viewed from the right-front side. Thus, the trays 107 conveyed from the left to the right in FIG. 1 is similarly conveyed from the left to the right in FIGS. 2 and 3.

The tray conveyor 106 disposed at the lower part of the medicine dispensing unit 103 is constituted by a combination of a plurality of conveyor belts.

Specifically, as shown in FIG. 2, the tray conveyor 106 has a first conveyor 201, the second conveyor 202, and a third conveyor 203.

The first conveyor 201 has a roller, a belt, and a motor for driving the roller. The motor is driven by receiving commands from a computer or other such control device (not shown), thereby conveying the trays 107.

The first conveyor 201 is located on the upstream side of the medicine dispensing unit 103, receives the trays 107 conveyed from the empty tray unit 102 side, and passes the trays over to the second conveyor 202. When a tray 107 stays on the second conveyor 202, the first conveyor 201 is controlled so as to hold back the tray 107 on the first conveyor 201.

The second conveyor 202 itself moves at a right angle to the conveyance direction of the trays 107, or the second conveyor 202 itself turns. A dispenser unit including a container takeout head 401 (shown in FIG. 4) and the other components is provided on the second conveyor 202, and the proper drugs can be issued in the desired regions of the trays 107 by combining the operations of moving, turning, and dispensing.

The configuration of the second conveyor 202 will be described in detail through reference to FIG. 3.

The second conveyor 202 is both a moving component for moving the trays 107 to the dispenser side, and a turning component for rotating the trays 107. The operations of moving and turning are not limited to what is described below, so long as the trays 107 can be moved at a right angle to the conveyance direction or turned.

The second conveyor 202 has a roller 205, a belt 206, and a motor 207. Thus, the drive force of the motor 207 is transmitted to the roller 205, which rotates the endless belt 206 and allows the trays 107 carried on the belt 206 to be conveyed in the desired direction.

The second conveyor 202 is disposed between the first conveyor 201 and the third conveyor 203, receives the trays 107 from the first conveyor 201, and passes them on to the third conveyor 203.

The second conveyor 202 has a turning component 208, a motor 209, a belt 210, and a roller 211. When the drive force of the motor 209 is transmitted through the roller 211 via the belt 210 and the roller 211 to the turning component 208, the turning component 208 turns. This causes the entire second conveyor 202 to rotate horizontally along with the trays 107 put on the upper face of the second conveyer 202

The second conveyor 202 is also provided with a motor 212, a ball screw 213, and a rail member 214. When the drive force of the motor 212 is transmitted to the ball screw 213, the rotational motion of the motor 212 is converted into linear motion. This allows the entire second conveyor 202 to move in a direction (the direction of the arrow in FIG. 3) that is perpendicular to the conveyance path of the trays 107 from the first conveyor 201 to the third conveyor 203.

The third conveyor 203 is similar to the first conveyor 201 in that it has a roller, a belt, and a motor for driving the roller. The third conveyor 203 receives a command from a computer or other such control device (not shown) to drive the motor, and conveys the trays 107 containing medicine. The third conveyor 203 is disposed downstream of the medicine dispensing unit 103, and delivers the trays 107 holding medicine containers 1, 2, and 3 to a conveyor disposed below the printer unit 104 and the filled tray unit 105.

An electronic card writing device 204 is provided along the third conveyor 203. In the electronic card writing device 204, patient information such as the date, patient's name, hospital ward, hospital room, and patient ID is written to a patient card (electronic card) provided on a side face of the trays 107, and this information is displayed on a display portion on the patient card.

Information such as prescription details and the kind of prescribed medicine may be written to the patient card at the same time as the above-mentioned information.

The electronic card writing device 204 may be provided to the first conveyor 201 or to the tray conveyor 106 at the lower part of the printer unit 104.

Next, the configuration of the means for dispensing the medicine containers 1, 2, and 3 will be described in detail through reference to FIG. 4.

Figure 4:
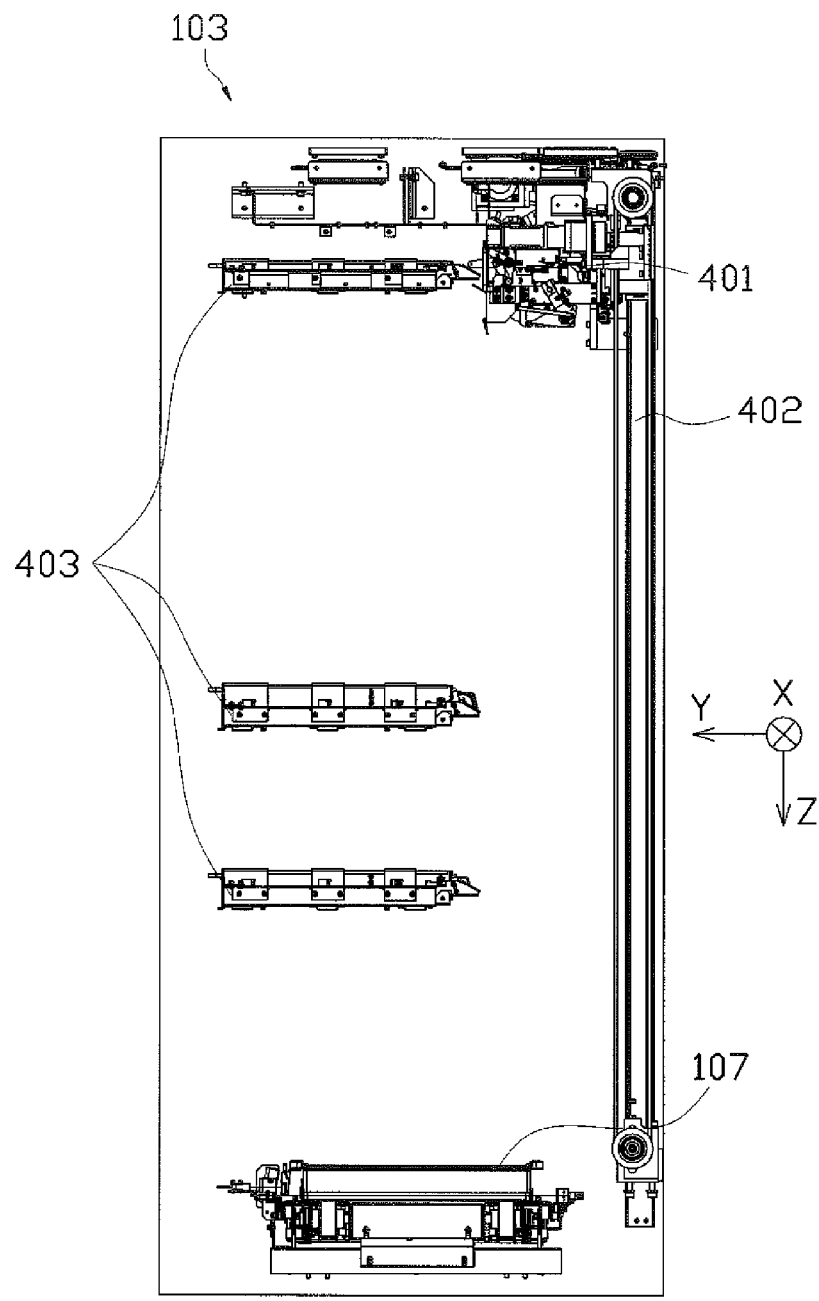
FIG. 4 is a side view of the configuration of the main parts of the medicine issuing device in FIG. 1.

FIG. 4 is a side view of the inside of the medicine dispensing unit 103 included in the medicine issuing device 101.

In FIG. 4, the X direction is away from the viewer, the Z direction is downward, and the Y direction is to the left.

Figure 5:
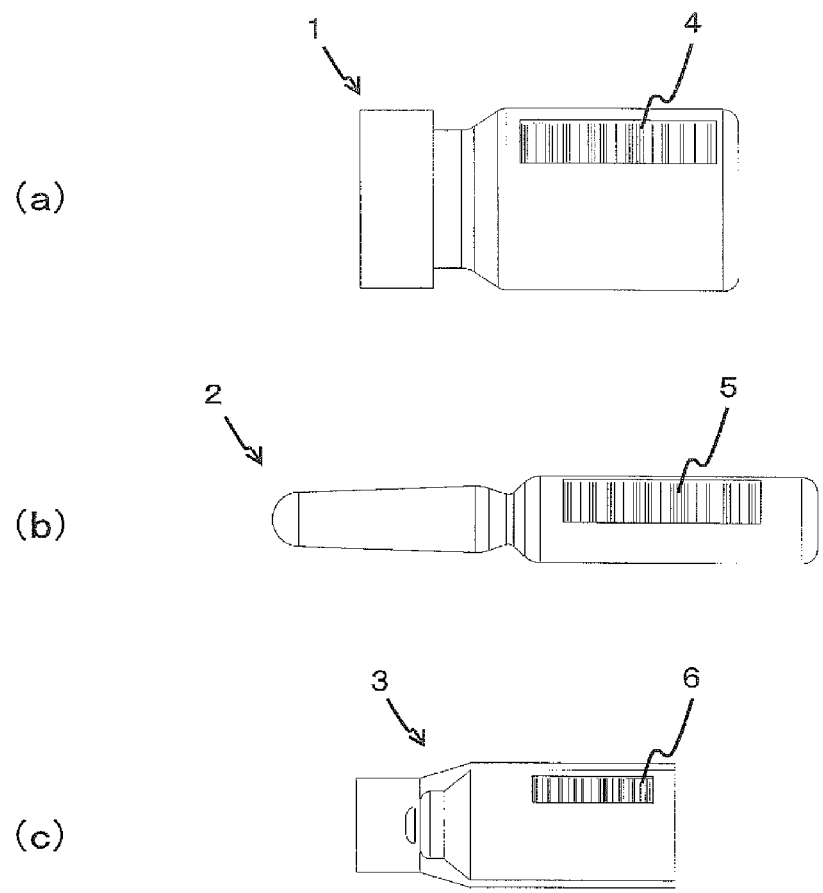
FIGS. 5a, 5b, and 5c are front views of a medicine container handled by the medicine issuing device in FIG. 1.
Figure 6:
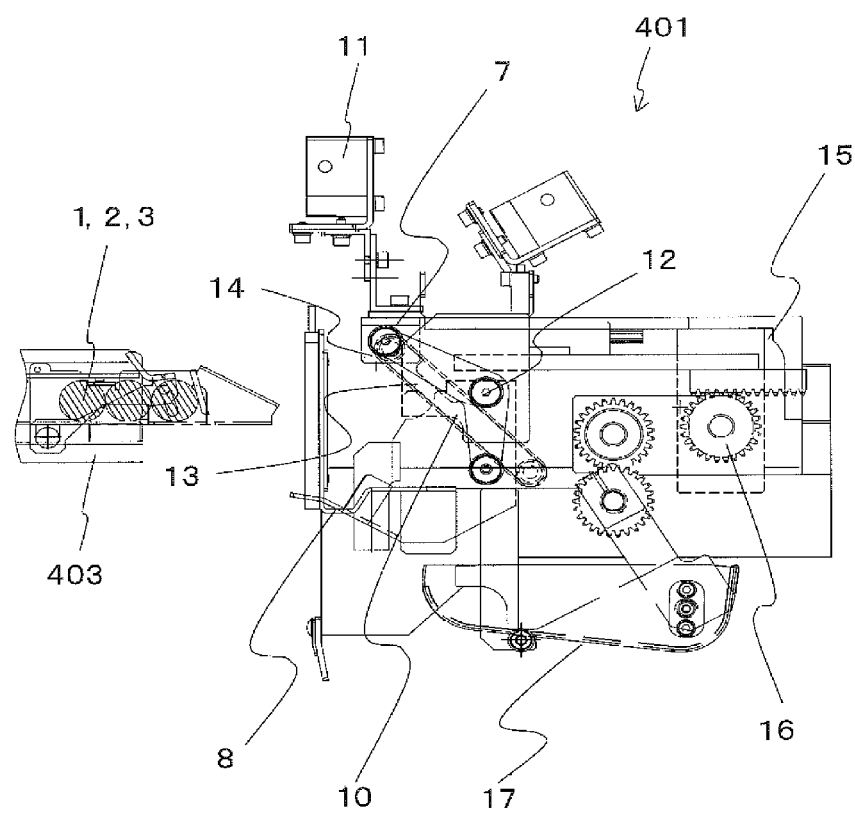
FIG. 6 is a side view of the container removal head of the medicine issuing device in FIG. 1.

The medicine dispensing unit 103 consists of a container takeout head 401 that takes the medicine containers 1, 2, and 3 shown in FIGS. 5a, 5b, and 5c out of the cassettes 403 shown in FIG. 6 and puts them in the trays 107, a head conveyor 402 that moves the container takeout head 401 in the XZ directions and thereby takes out the medicine containers 1, 2, and 3 loaded into the cassettes 403, and a plurality of cassettes 403 into which the medicine containers 1, 2, and 3 are loaded by the type of medicine.

Specifically, in this embodiment, the medicine containers 1, 2, and 3 are each held in their own cassette 403.

The container takeout head 401 is moved by the head conveyor 402 to near the cassette 403 containing the desired one of the medicine containers 1, 2, and 3, on the basis of a pharmaceutical from a computer (not shown). The desired one of the medicine containers 1, 2, and 3 is received from the cassette 403, and the container takeout head 401 is moved back so as to be directly over a tray 107 by the head conveyor 402, after which one of the medicine containers 1, 2, and 3 is dispensed onto the tray 107.

The medicine containers 1, 2, and 3 that are dispensed into the trays 107 by the container takeout head 401 will now be described.

The medicine containers 1, 2, and 3 each hold a different medicine. The medicine containers 1, 2, and 3 are tubular in shape, and identifying marks 4, 5, and 6 are provided to the outer periphery thereof. To describe this in further detail, the medicine containers 1, 2, and 3 are each tubular in shape, but have different diameters. The identifying marks 4, 5, and 6 are provided along the lengthwise direction of the medicine containers 1, 2, and 3, on part of the outer peripheral face of the medicine containers 1, 2, and 3.

As discussed above, the medicine containers 1, 2, and 3 are each held in a different cassette 403, and are taken out of the cassettes 403 by the container takeout head 401 as shown in FIGS. 6 to 13 (discussed below).

Figure 7:
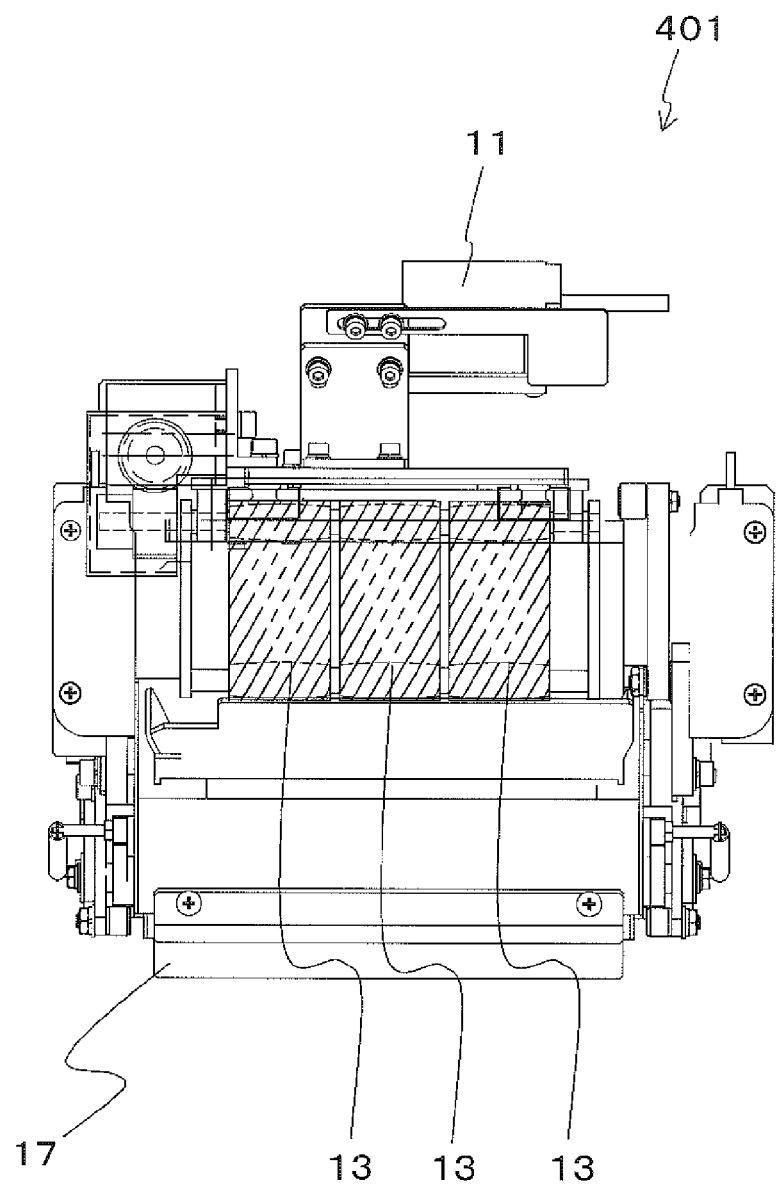
FIG. 7 is a front view of the container removal head in FIG. 6.

As shown in FIGS. 6 and 7, the container takeout head 401 comprises an operation component 7, a movement path component 8, a container rotation component 10, and an identifying mark reader 11.

The operation component 7 takes out one of the medicine containers 1, 2, and 3 from its cassette 403. The operation component 7 also rotates either clockwise or counter-clockwise around a rotational shaft 12.

Figure 12:
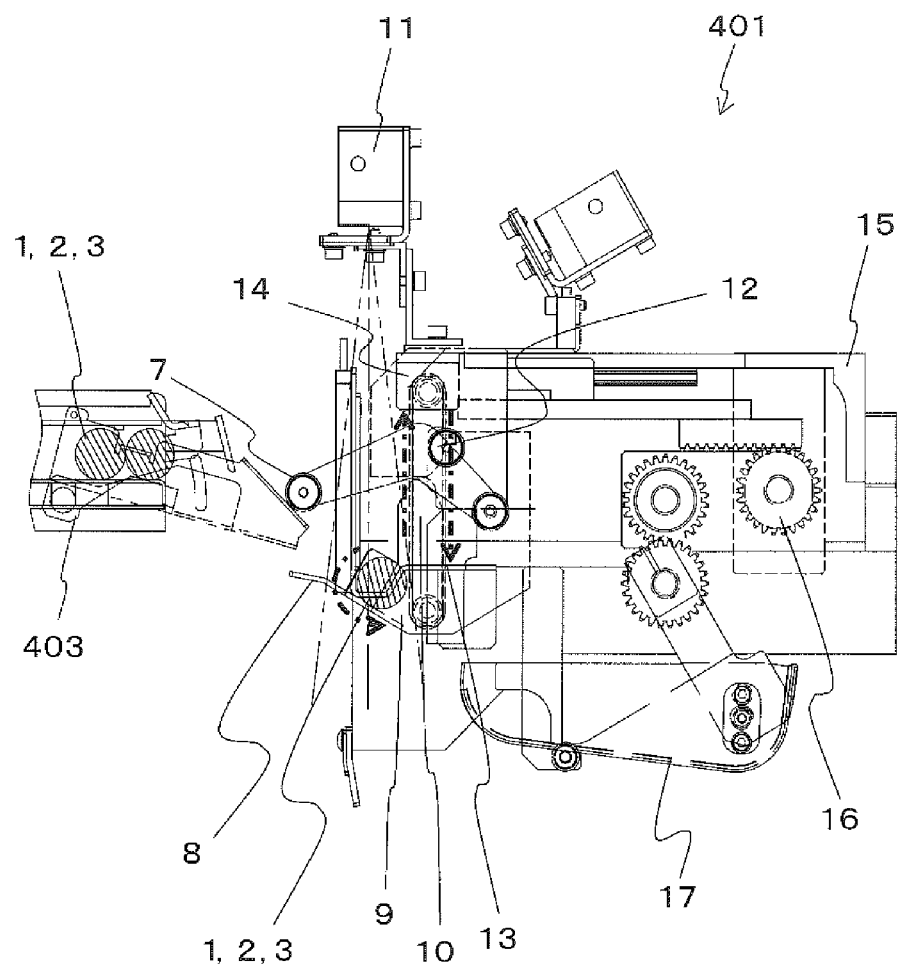
FIG. 12 is a side view of the container removal head in FIG. 6.

The movement path component 8 moves one of the medicine containers 1, 2, and 3 taken out by the operation component 7 to an identification position 9 (see FIG. 12). The movement path component 8 has a downward sloping face that causes the tubular medicine containers 1, 2, and 3 to roll under their own weight (gravity).

The container rotation component 10 rotates one of the medicine containers 1, 2, and 3 moved via the movement path component 8 to the identification position 9, around its outer peripheral face at the identification position 9, until one of the identifying marks 4, 5, and 6 provided to the outer peripheral face of the medicine containers 1, 2, and 3 is read by the identifying mark reader 11. The container rotation component 10 has a belt (stopper) 13 that temporarily stops the oblique movement of the medicine containers 1, 2, and 3 moving in the slope direction of the movement path component 8, and a motor 14 (rotation component) that rotates the medicine containers 1, 2, and 3, whose oblique movement has been temporarily stopped by the belt 13, around the outer peripheral face.

Here, the medicine containers 1, 2, and 3 rotated by the container rotation component 10 rotate around the outer peripheral face at the specific identification position 9 in a state of being in contact with the belt 13. In other words, the medicine containers 1, 2, and 3 rotate along with the rotation of the belt 13 around the center axis of the tubular medicine containers 1, 2, and 3.

The belt 13 consists of a rubber belt, and as shown in FIG. 7, a plurality of belts 13 are disposed at a specific spacing in order to catch the medicine containers 1, 2, and 3 that roll down the movement path component 8. The belt 13 holds the medicine containers 1, 2, and 3 in a state of being in contact with the outer peripheral face of the medicine containers 1, 2, and 3 whose rolling has been stopped.

The identifying mark reader 11 reads the identifying marks 4, 5, and 6 on the medicine containers 1, 2, and 3 that are rotated at the identification position 9 by the container rotation component 10.

In the above configuration, the medicine issuing device 101 in this embodiment is such that the operation component 7, the movement path component 8, the container rotation component 10, and the identifying mark reader 11 are mounted to the base 15 shown in FIG. 6.

The base 15 rotates a gear 16 counter-clockwise, and thereby moves closer to the cassettes 403 that are fixed inside the medicine dispensing unit 103.

FIGS. 6 and 7 show a state in which the base 15 has been moved in front of the cassette 403 holding one of the medicine containers 1, 2, and 3 that is being taken out by the container takeout head 401.

Figure 8:
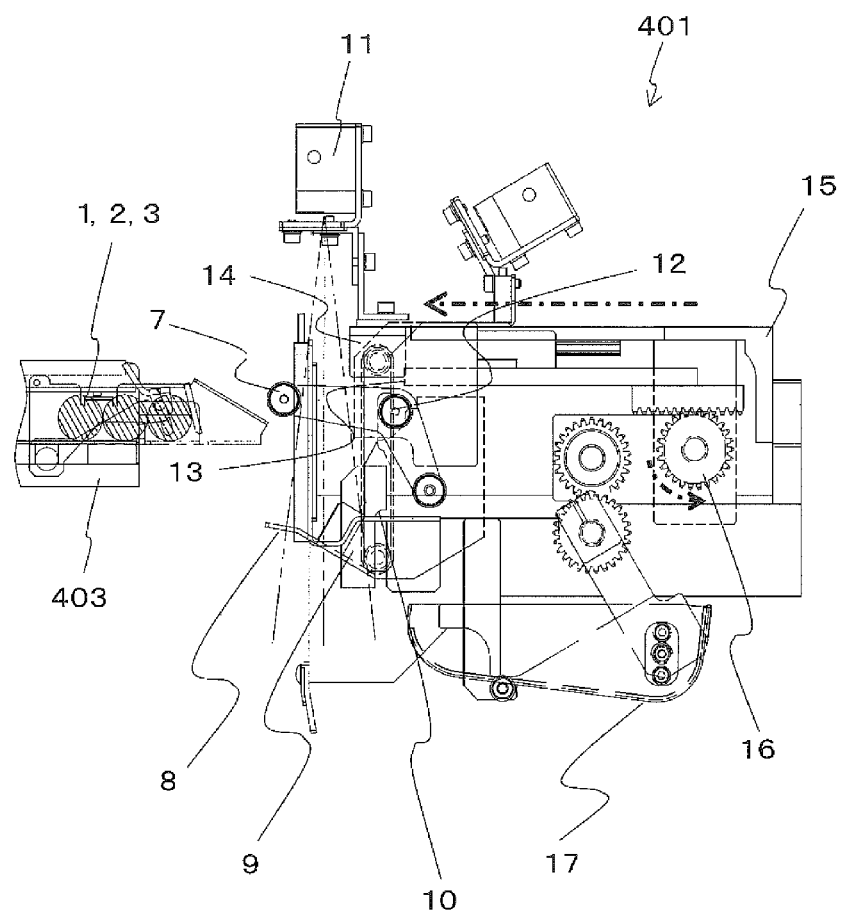
FIG. 8 is a side view of the container removal head in FIG. 6.
Figure 9:
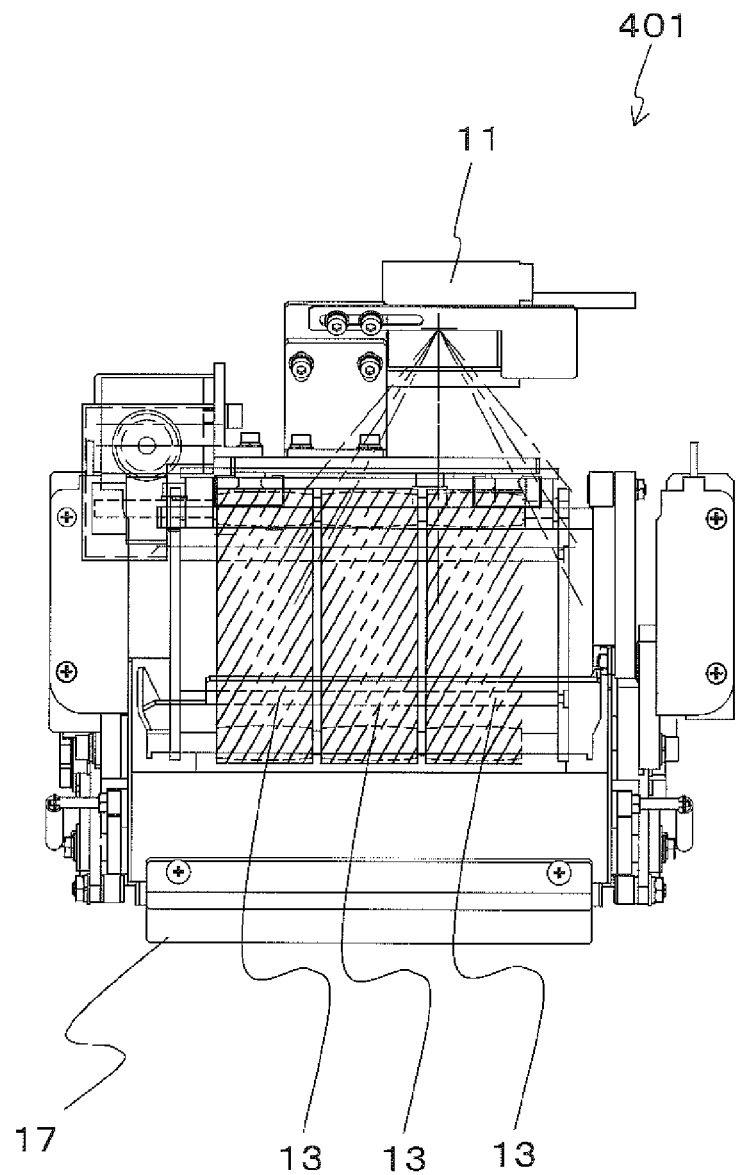
FIG. 9 is a front view of the container removal head in FIG. 6.

At this point, the operation component 7 is located above the cassette 403. The lower part of the container rotation component 10 is located away from the cassette 403 (away from the movement path component 8). In this state, when the gear 16 rotates counter-clockwise, the base 15 moves toward the cassette 403 as shown in FIGS. 8 and 9. Then, in a state in which the base 15 has moved to the position shown in FIGS. 8 and 9, the lower part of the container rotation component 10 moves closer to the movement path component 8.

Consequently, the above-mentioned identification position 9 is formed between the lower part of the movement path component 8 and the lower part of the container rotation component 10. That is, the container rotation component 10 is able to move toward and away from the movement path component 8, and the container rotation component 10 can be moved closer to the movement path component 8 before one of the medicine containers 1, 2, and 3 is taken out from the cassette cassettes 403 by the operation component 7. This allows the identification position 9 to be formed at a specific location on the downstream side of the movement path component 8.

Figure 10:
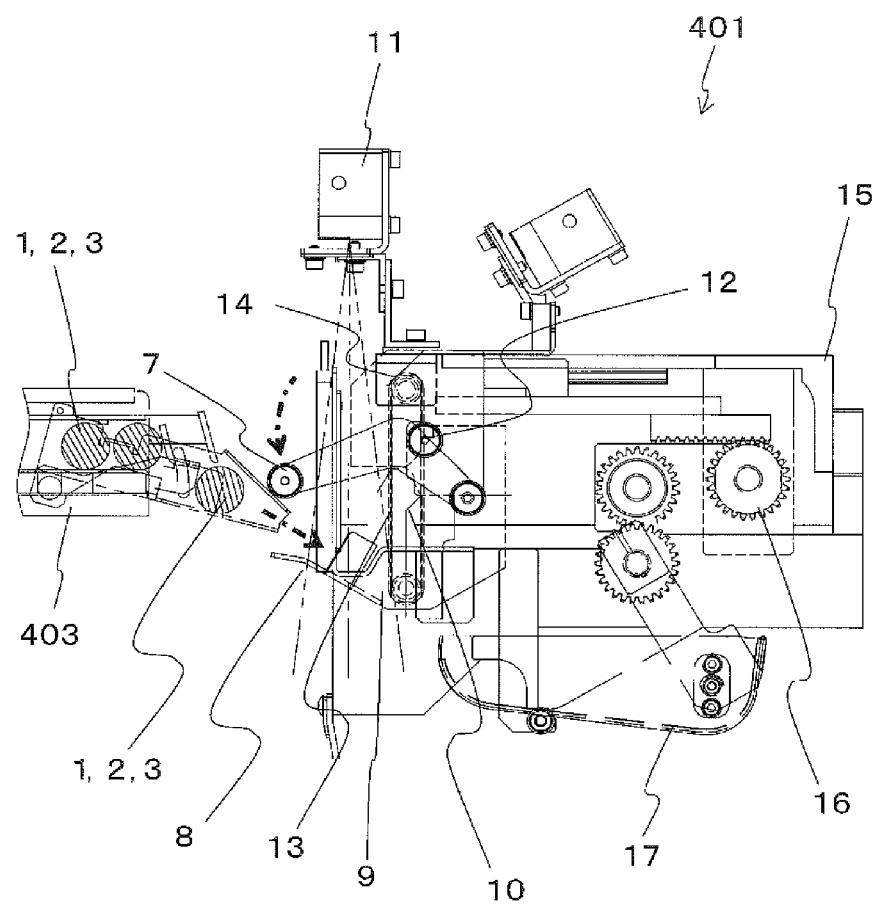
FIG. 10 is a side view of the container removal head in FIG. 6.
Figure 11:
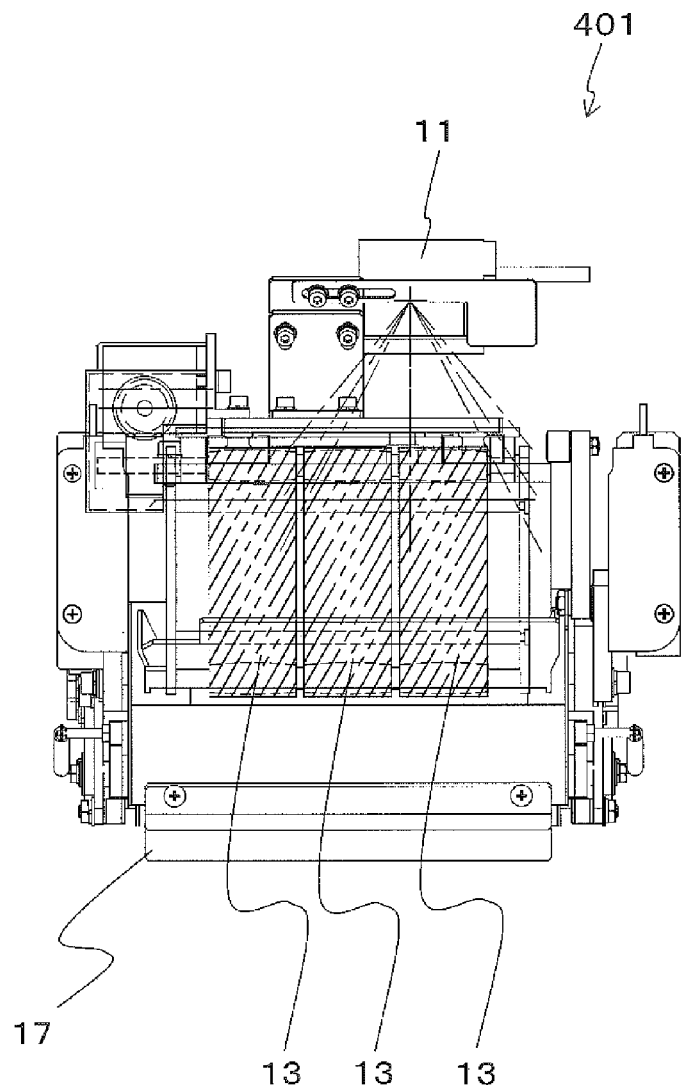
FIG. 11 is a front view of the container removal head in FIG. 6.

As shown in FIGS. 10 and 11, the operation component 7 is then rotated counter-clockwise to operate the cassette 403.

Figure 13:
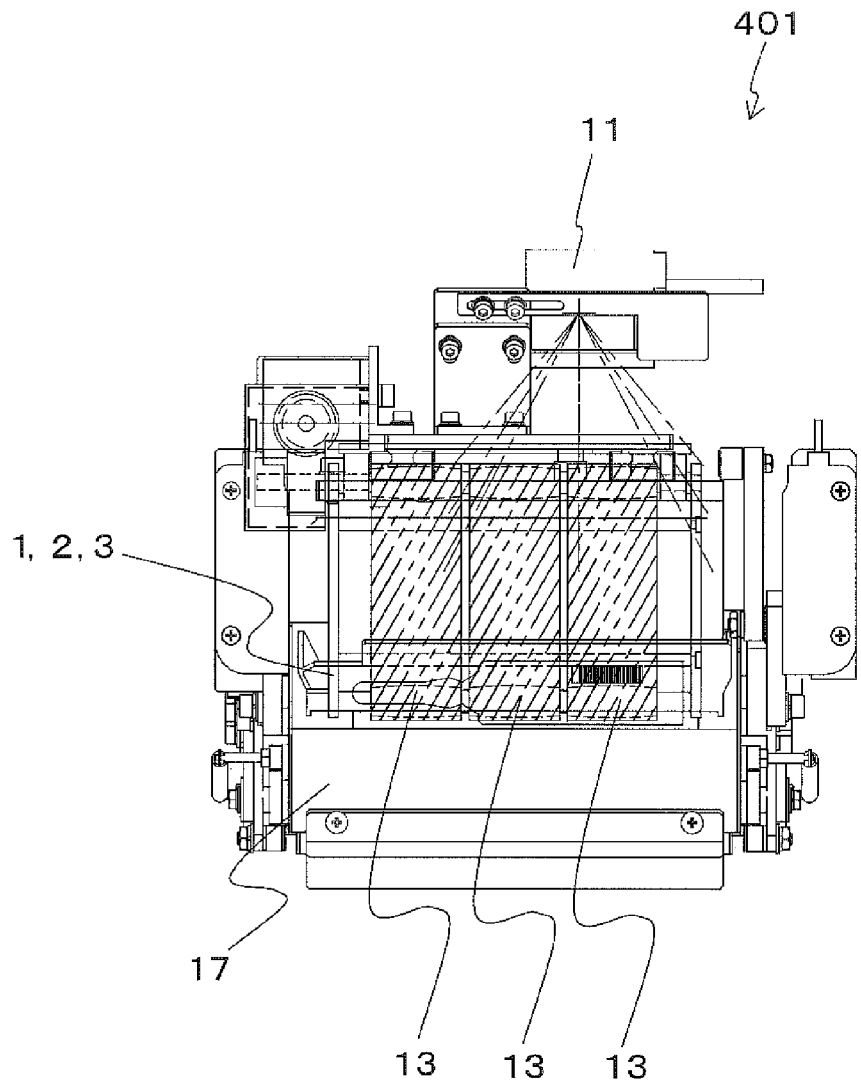
FIG. 13 is a front view of the container removal head in FIG. 6.

This operation has been well known for some time, and if the cassette 403 is operated by the operation component 7, just one of the medicine containers 1, 2, and 3 will be taken out of the cassette 403, as shown in FIGS. 12 and 13. The medicine container 1, 2, or 3 taken out of the cassette 403 then rolls down the downward sloped face of the movement path component 8 to the identification position 9.

Specifically, as shown in FIG. 5, since the medicine containers 1, 2, and 3 are all tubular around the outside, they roll down the downward sloped face of the movement path component 8.

In this embodiment, before the rolling of the medicine container 1, 2, or 3, the belts 13 that constitute the container rotation component 10 move closer to the lower part of the movement path component 8.

Therefore, the medicine containers 1, 2, and 3 that roll down the downward sloped face of the movement path component 8 come into contact with the belts 13, which stops the downward movement.

The belts 13 here are rubber belts, and are disposed in a state of being separated at a specific spacing (a gap through which none of the medicine containers 1, 2, and 3 will pass). Therefore, the belts 13 can exert a sufficient cushioning action on the medicine containers 1, 2, and 3. Consequently, when the medicine containers 1, 2, and 3 that have rolled down the downward sloped face of the movement path component 8 hit the belts 13, there will be no damage to the medicine containers 1, 2, and 3.

Next, with the medicine issuing device 101 in this embodiment, one of the medicine containers 1, 2, and 3 rotates in a state in which its downward rolling has been stopped, at the identification position 9 formed at the lower part of the movement path component 8. The identifying marks 4, 5, or 6 provided to the outer peripheral face of the rotating medicine container 1, 2, or 3 are read by the identifying mark reader 11. That is, the identification position 9 is formed by the lower part of the movement path component 8 and the lower part of the container rotation component 10 shown in FIGS. 12 and 13, and the identifying mark 4, 5, or 6 is read by the identifying mark reader 11.

As shown in FIGS. 5a to 5c, the identifying marks 4, 5, and 6 provided to the outer peripheral face of the medicine containers 1, 2, and 3 are provided along the lengthwise direction of only a part of the outer peripheral face. Therefore, these identifying marks 4, 5, and 6 may not always be facing the identifying mark reader 11.

In view of this, with the medicine issuing device 101 in this embodiment, the medicine containers 1, 2, and 3 that have rolled to the identification position 9 are rotated by the belts 13 of the container rotation component 10 that they hit, which rotates them in place around their center axis and around the outer peripheral face.

More specifically, the belts 13 that constitute the container rotation component 10 are rotated clockwise (in FIGS. 12 and 13), which rotates the medicine containers 1, 2, and 3 counter-clockwise. Furthermore, in this embodiment, the rotation of the belts 13 is continued until the reading of the identifying marks 4, 5, and 6 by the identifying mark reader 11 is complete. In other words, once the reading of the identifying marks 4, 5, and 6 by the identifying mark reader 11 is complete, the rotation of the belts 13 is halted. That is, in this embodiment, it is possible that the medicine containers 1, 2, and 3 will be rotated more than 360 degrees at the identification position 9 by the time the reading of the identifying marks 4, 5, and 6 by the identifying mark reader 11 is complete.

Consequently, this creates a state in which the identifying marks 4, 5, and 6 on the medicine containers 1, 2, and 3 are facing the identifying mark reader 11 at the identification position 9. This allows the identifying marks 4, 5, and 6 to be reliably read by the identifying mark reader 11.

That is, even if a different type of medicine container should be accidentally placed in the cassettes 403 in which the medicine containers 1, 2, and 3 have been loaded by type, the identifying marks 4, 5, and 6 provided to the outer peripheral face of the medicine containers 1, 2, and 3 taken out of the cassettes 403 can still be properly read by the identifying mark reader 11. This allows recognition of whether or not the proper medicine containers 1, 2, and 3 have been taken out at the identification position 9 just before the dispensing into a holder 17. As a result, the desired medicine containers 1, 2, and 3 corresponding to a prescription, etc., can be collected very accurately in the trays 107.

In this embodiment, because the movement path component 8 is provided, a state that is close to an acute angle (less than 90 degrees) is formed between the movement path component 8 and the belts 13 constituting the container rotation component 10. In this state, the medicine containers 1, 2, and 3 can be rotated counter-clockwise by rotating the belt 13 clockwise.

More precisely, when the belts 13 constituting the container rotation component 10 are rotated counter-clockwise so as to rotate the medicine containers 1, 2, and 3 clockwise, there is the risk that the medicine containers 1, 2, and 3 that have rolled clockwise will end up being sandwiched between the movement path component 8 and the belts 13 constituting the container rotation component 10.

In view of this, in this embodiment, as discussed above, the belts 13 constituting the container rotation component 10 are rotated clockwise, and are further rotated outward the way the medicine containers 1, 2, and 3 are discharged, with respect to the acute angle formed between the movement path component 8 and the belts 13 constituting the container rotation component 10.

This prevents the medicine containers 1, 2, and 3 from being sandwiched between the downward sloped face of the movement path component 8 and the belts 13, and allows the medicine containers 1, 2, and 3 to be properly rotated at the identification position 9. As a result, the identifying marks 4, 5, and 6 on the medicine containers 1, 2, and 3 can be reliably read by the identifying mark reader 11.

Figure 14:
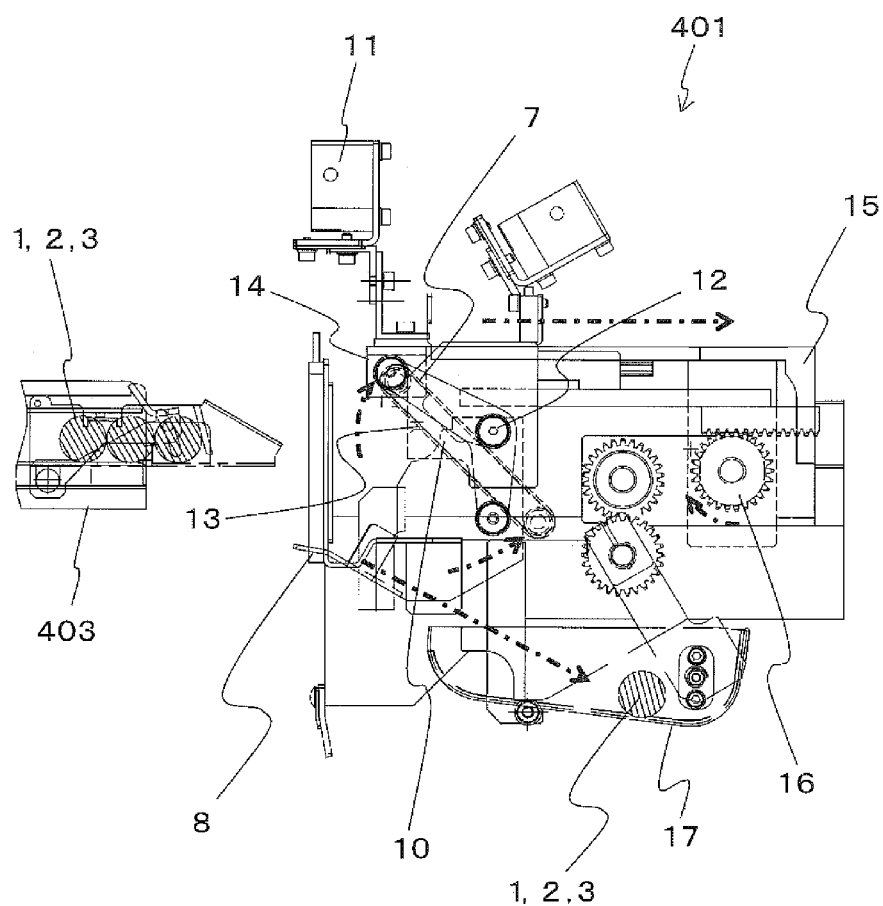
FIG. 14 is a side view of the container removal head in FIG. 6.
Figure 15:
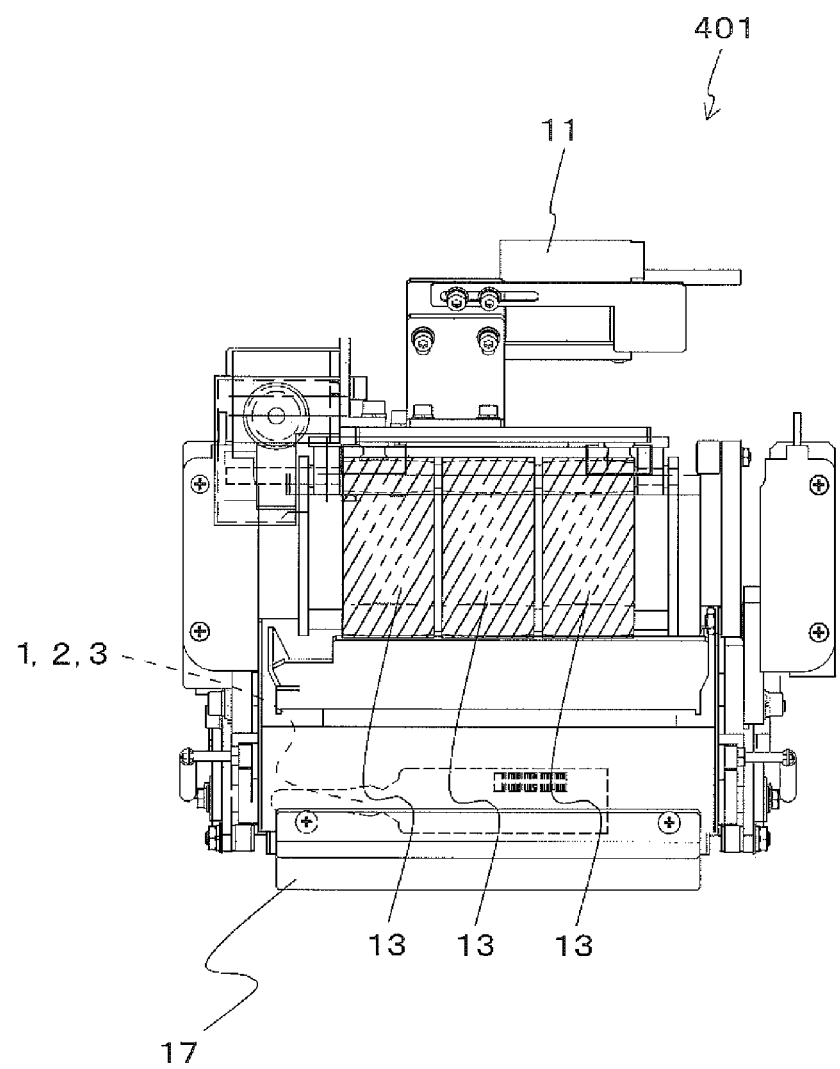
FIG. 15 is a front view of the container removal head in FIG. 6.

FIGS. 14 and 15 show a state in which the medicine containers 1, 2, and 3, whose identification by the identifying mark reader 11 has been completed, are moved to the holder 17.

That is, when the gear 16 is rotated clockwise from the state shown in FIGS. 12 and 13, a large gap is formed at the lower part of the movement path component 8, and the identification position 9 is released, by rotating the lower part of the container rotation component 10 counter-clockwise before the base 15 starts to move away from the cassette 403.

Then, the medicine containers 1, 2, and 3 held at the identification position 9 roll down the downward sloped face of the movement path component 8 into the holder 17 provided at the lower part of the movement path component 8.

After this, the container takeout head 401 is moved by the head conveyor 402 shown in FIG. 4 to the tray 107.

Figure 16:
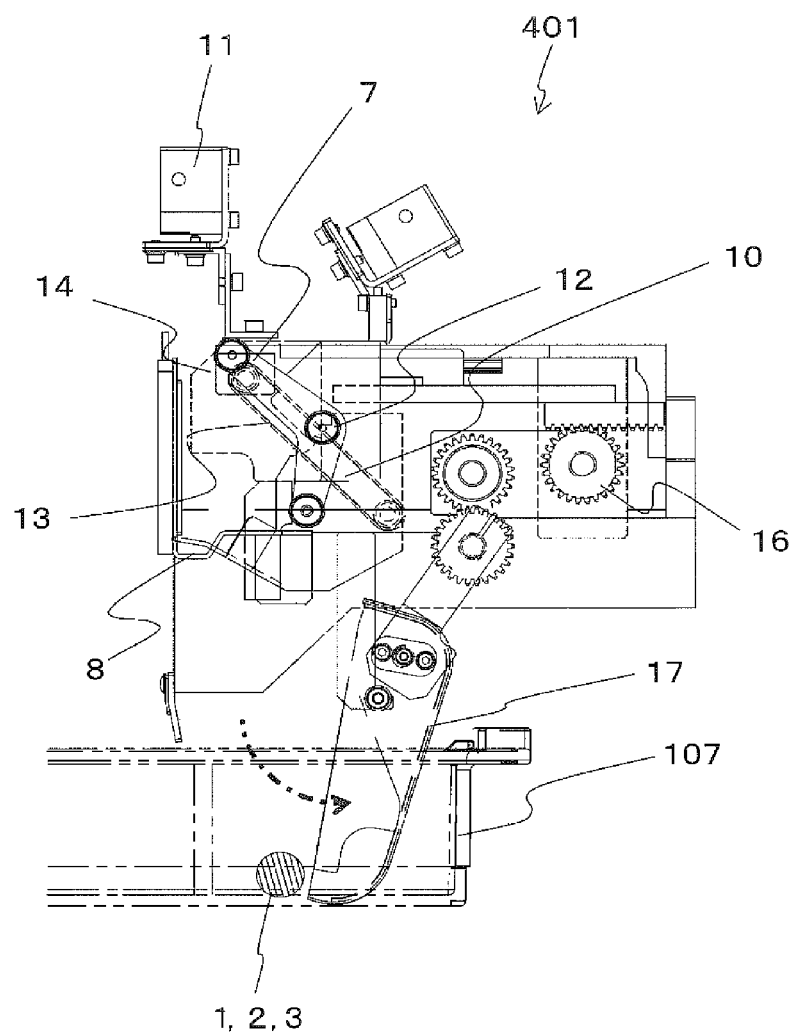
FIG. 16 is a side view of the container removal head in FIG. 6.

Then, as shown in FIG. 16, the holder 17 is opened toward the tray 107 below. This places the medicine containers 1, 2, and 3 in the tray 107.

When the identifying mark reader 11 reads the identifying marks 4, 5, and 6 provided to the outer peripheral face of the medicine containers 1, 2, and 3 rotating at the identification position 9, if a medicine container is recognized which is different from the medicine container that was supposed to be taken out of the cassette 403, the system may be controlled, for example, so that that medicine container is dispensed into a waste tray (not shown) provided at a separate location from that of the tray 107.

Alternatively, if there is a medicine container that has been taken out accidentally, it may be left in the tray 107, a "NG" mark indicating that the wrong medicine has been dispensed is noted on the prescription or the like produced by the printer unit 104, and the medicine is dispensed into the tray 107. In this case, when the medicines dispensed by the medicine issuing device 101 are checked, the medicine container that was incorrectly dispensed should be taken out by a nurse, etc., and replaced with the proper medicine container.

Embodiment 2

A medicine issuing device 501 pertaining to another embodiment of the present invention will now be described through reference to FIGS. 17 and 18.

The medicine issuing device 501 in this embodiment is substantially the same as the medicine issuing device 101 in Embodiment 1 above, except that an auxiliary roller 503 that assists the rotation of the medicine containers 1, 2, and 3 is provided near the identification position 9 where the identifying marks 4, 5, and 6 of the medicine containers 1, 2, and 3 are read. Thus, in this embodiment those members having the same function as in the above embodiment will be numbered the same, and will not be described again in detail.

Figure 17:
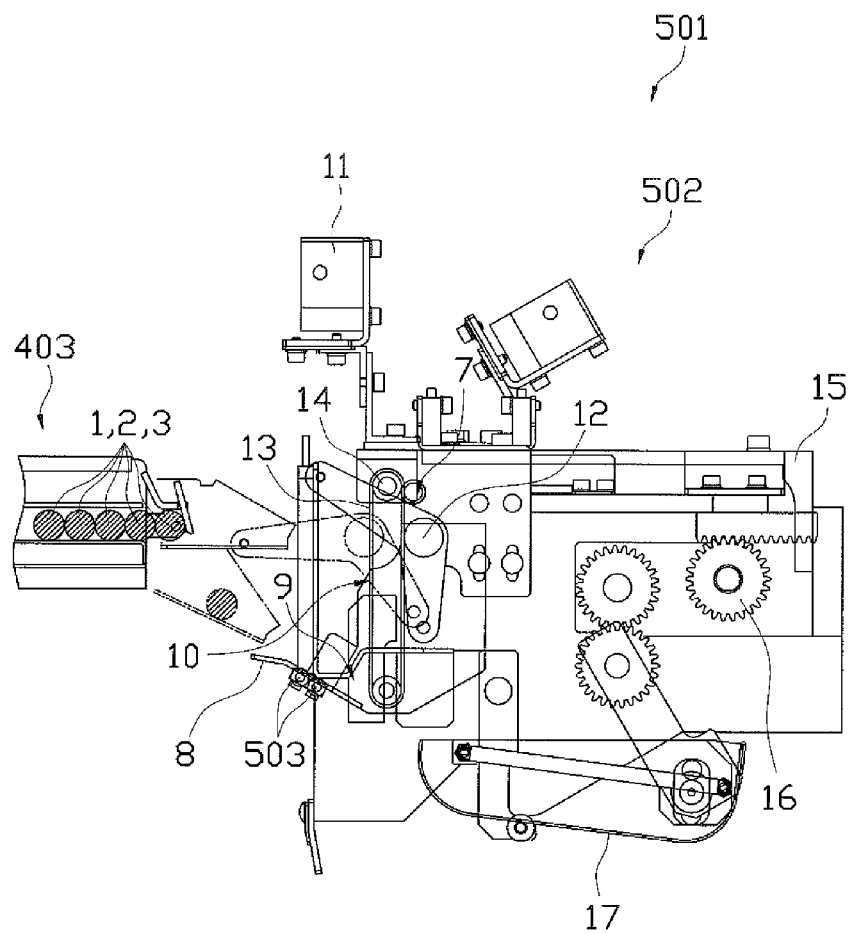
FIG. 17 is a side view of the configuration of the main parts of the medicine issuing device pertaining to another embodiment of the present invention.

As shown in FIG. 17, the medicine issuing device 501 in this embodiment comprises a plurality of auxiliary rollers 503 provided to the movement path component 8 within a container removal head 502, so as to support the medicine containers 1, 2, and 3 from below at the identification position 9.

Specifically, the auxiliary rollers 503 are freely rotating rollers that have no drive source, and are provided to the movement path component 8 so as to hit from below the outer peripheral face of the medicine containers 1, 2, and 3 supported at the identification position 9.

Figure 18:
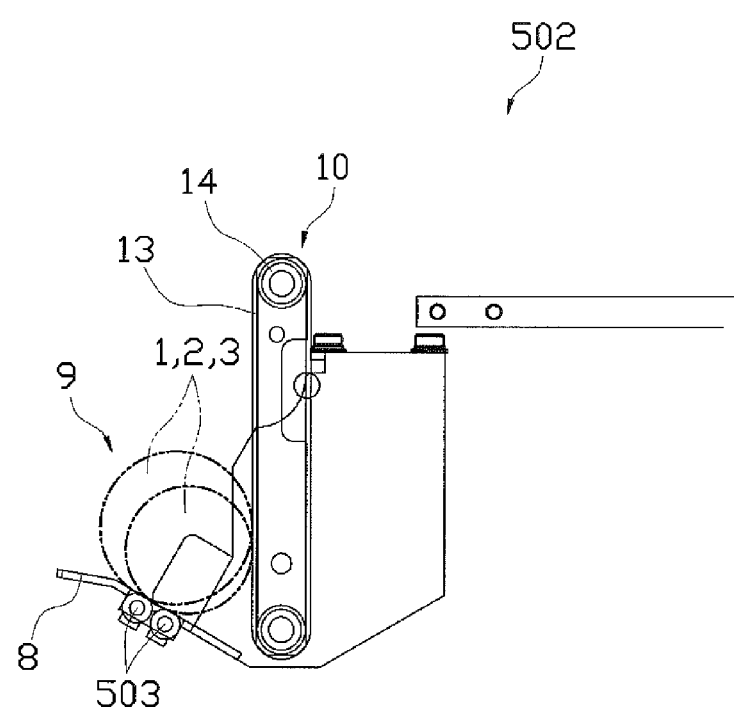
FIG. 18 is a side view of the configuration of the main parts in FIG. 17.

As shown in FIG. 18, the result is that the medicine containers 1, 2, and 3 can be supported from below at two points in a state in which medicine containers 1, 2, and 3 of different diameters are held at the identification position 9. Thus, when the medicine containers 1, 2, and 3 are rotated counter-clockwise by clockwise rotation of the belts 13 in a state of contact with the belts 13 at the identification position 9, there is less wear resistance on the movement path component 8, and the medicine containers 1, 2, and 3 can be easily rotated in the desired direction.

Other Embodiments

Embodiments of the present invention were described above, but the present invention is not limited to or by the above embodiments, and various modifications are possible without departing from the gist of the invention.

(A)

In the above embodiments, an example was given in which the container rotation component 10 was moved toward and away from the movement path component 8 by rotating the motor 14, but the present invention is not limited to this.

For example, this motor 14 may be used to drive the operation component 7. Of course, a motor that drives the operation component 7 (not shown) may be provided separately. Also, a motor that rotates the gear 16 (not shown) may be used to rotate the holder 17.

(B)

In the above embodiments, the medicine issuing device 101 was described which took out the medicine containers 1, 2, and 3 and identified them, but the present invention is not limited to this.

For example, the present invention can also be applied to a container identifying device that takes out and identifies containers filled with something other than medicine.

(C)

In Embodiment 2 above, an example was given in which two of the auxiliary rollers 503 were provided for assisting the rotation of the medicine containers 1, 2, and 3 at the identification position 9, but the present invention is not limited to this.

For example, the number of auxiliary rollers may be something other than two, such as just one, or three or more.

INDUSTRIAL APPLICABILITY

The present invention has the effect of allowing removed containers to be identified by type very accurately, and can therefore be widely applied to medicine issuing devices and so forth.

REFERENCE SIGNS LIST 1, 2, 3 medicine container (container)
4, 5, 6 identifying marks
7 operation component
8 movement path component
9 identification position
10 container rotation component
11 identifying mark reader
12 rotational shaft
13 belt (stopper)
14 motor (rotation component)
15 base
16 gear
17 holder
101 medicine issuing device (container identifying device)
102 empty tray unit
103 medicine dispensing unit
104 printer unit
105 filled tray unit
106 tray conveyor
107 tray
201 first conveyor
202 second conveyor
203 third conveyor
204 electronic card writing device
205 roller
206 belt
207 motor
208 turning component
209 motor
210 belt
211 roller
212 motor
213 ball screw
214 rail member
401 container takeout head
402 head conveyor
403 cassette
501 medicine issuing device
502 container removal head
503 auxiliary roller

The invention claimed is:

1. A medicine issuing device, comprising:
a cassette in which are loaded a plurality of tubular medicine containers provided with identifying marks on the outer peripheral face of the tubular medicine containers;
an operation component configured to take the medicine containers out of the cassette;
a movement path component configured to move the medicine containers taken out by the operation component to a specific identification position;
a container rotation component configured to rotate the medicine containers around the outer peripheral face until the reading of the identifying marks on the medicine containers is complete at the identification position; and
an identifying mark reader configured to read the identifying marks on the medicine containers rotated by the container rotation component;
wherein the movement path component has a downward slope that causes the tubular medicine containers to roll under their own weight; and
wherein the container rotation component has:
a stopper configured to temporarily stop the movement of the medicine containers moving in the slope direction of the movement path component; and
a rotation component configured to rotate the medicine containers, whose movement in the slope direction has been temporarily stopped by the stopper, around the outer peripheral face at that position.

2. The medicine issuing device according to claim 1, further comprising a placement component configured to place the medicine containers taken out by the operation component into a tray.

3. The medicine issuing device according to claim 1, further comprising an auxiliary roller configured to assist the rotation of the medicine containers, at the identification position.

4. The medicine issuing device according to claim 1, wherein the container rotation component rotates the medicine containers in the opposite direction from the rolling direction of the medicine containers in the movement path component.

5. The medicine issuing device according to claim 1, wherein the stopper has a belt configured to catch the medicine containers that have rolled down on the movement path component, and
the rotation component has a motor configured to rotate the belt.

6. The medicine issuing device according to claim 1, wherein the stopper has a plurality of belts configured to catch the containers rolling down the movement path component, and
the belts are disposed spaced a specific distance apart, and come into contact with the outer peripheral part of the medicine containers.

7. The medicine issuing device according to claim 1, wherein the belt is a rubber belt.

8. The medicine issuing device according to claim 1, wherein the container rotation component is able to move with respect to the movement path component, and moves the container rotation component closer to the movement path component prior to when the medicine containers are taken out of the cassette by the operation component.

9. The medicine issuing device according to claim 1, comprising a container removal head that includes the operation component, the container rotation component, the identifying mark reader, and the movement path component.

10. A container identifying device for identifying a tubular container provided with an identifying mark on its outer peripheral face, said container identifying device comprising:
an operation component configured to take a medicine container out of a cassette filled in with a plurality of the medicine containers;
a movement path component configured to move the containers taken out by the operation component to a specific identification position;
a container rotation component configured to rotate the containers around the outer peripheral face of the containers until the reading of the identifying marks on the containers is complete at the identification position; and
an identifying mark reader configured to read the identifying marks on the containers rotated by the container rotation component;
wherein the movement path component has a downward slope that causes the tubular medicine containers to roll under their own weight; and
wherein the container rotation component has:
 a stopper configured to temporarily stop the movement in the slope direction of the containers moving in the slope direction of the movement path component; and
 a rotation component configured to rotate the containers, whose movement in the slope direction has been temporarily stopped by the stopper, around the outer peripheral face at that position.

11. The container identifying device according to claim 10, further comprising an auxiliary roller configured to assist the rotation of the containers, at the identification position.

12. The container identifying device according to claim 10, wherein the container rotation component rotates the containers in the opposite direction from the rolling direction of the containers in the movement path component.

13. The container identifying device according to claim 10, wherein the stopper has a belt configured to catch the containers that have rolled down the movement path component, and
the rotation component has a motor configured to rotate the belt.

14. The container identifying device according to claim 10, wherein the stopper has a plurality of belts configured to catch the containers rolling down the movement path component, and
the belts are disposed spaced a specific distance apart, and come into contact with the outer peripheral part of the containers.

15. The container identifying device according to claim 13, wherein the belt is a rubber belt.

16. The container identifying device according to claim 10, wherein the container rotation component is able to move with respect to the movement path component, and moves the container rotation component closer to the movement path component prior to when the containers are taken out of the cassette by the operation component.

17. The container identifying device according to claim 10, comprising a container removal head that includes the operation component, the container rotation component, the identifying mark reader, and the movement path component.

* * * * *